(12) United States Patent
Dimarco et al.

(10) Patent No.: US 7,258,024 B2
(45) Date of Patent: Aug. 21, 2007

(54) SIMPLIFIED FLUID PROPERTY MEASUREMENT

(75) Inventors: Steven J. Dimarco, Chanhassen, MN (US); Jeffry D. Foster, Minneapolis, MN (US); Mark S. Schumacher, Minneapolis, MN (US); Terry X. Beachey, Longmont, CO (US)

(73) Assignee: Rosemount Inc., Eden Prairie, MN (US)

( * ) Notice: Subject to any disclaimer, the term of this patent is extended or adjusted under 35 U.S.C. 154(b) by 124 days.

(21) Appl. No.: 11/090,923

(22) Filed: Mar. 25, 2005

(65) Prior Publication Data

US 2005/0210998 A1  Sep. 29, 2005

Related U.S. Application Data

(60) Provisional application No. 60/556,399, filed on Mar. 25, 2004.

(51) Int. Cl.
*G01F 1/32* (2006.01)

(52) U.S. Cl. .................................. 73/861.22

(58) Field of Classification Search ............. 73/861.22, 73/861.24, 861.61, 861.21
See application file for complete search history.

(56) References Cited

U.S. PATENT DOCUMENTS

| | | | |
|---|---|---|---|
| 3,370,463 A | 2/1968 | Chanaud | 73/194 |
| 3,638,037 A | 1/1972 | McMurtrie | 307/233 |
| 3,709,034 A | 1/1973 | Herzel | 73/194 B |
| 3,719,073 A | 3/1973 | Mahon | 73/194 B |
| 3,729,995 A | 5/1973 | Kovacs et al. | 73/194 B |
| 3,776,033 A | 12/1973 | Herzl | 73/194 B |
| 3,796,096 A | 3/1974 | Sielaff et al. | 73/194 |
| 3,864,972 A | 2/1975 | Burgess et al. | 73/194 B |
| 3,885,432 A | 5/1975 | Herzel | 73/194 B |
| 3,992,939 A | 11/1976 | November | 73/194 M |
| 4,010,645 A | 3/1977 | Herzl | 73/194 B |
| 4,026,150 A | 5/1977 | Schmidt | 73/194 VS |
| 4,048,854 A | 9/1977 | Herzl | 73/194 VS |
| 4,094,194 A | 6/1978 | Herzl | 73/194 VS |
| 4,142,407 A | 3/1979 | Kuroiwa et al. | 73/861.22 |
| 4,169,376 A | 10/1979 | Herzl | 73/194 VS |

(Continued)

FOREIGN PATENT DOCUMENTS

DE    287 995 A    3/1991

(Continued)

OTHER PUBLICATIONS

International Search Report and Written Opinion from International Application No. PCT/US2005/009915, filed Mar. 25, 2005.

*Primary Examiner*—Jewel Thompson
(74) *Attorney, Agent, or Firm*—Westman, Champlin & Kelly, P.A.

(57) ABSTRACT

A process fluid measurement system provides a first measurement relative to process fluid flowing in a pipe. An additional measurement of process fluid flow velocity in the pipe is combined with the first measurement to provide a simplified indication of mass fluid flow and/or density or other fluid parameter. In some embodiments, the first measurement is a differential pressure measurement. Additionally, one embodiment provides a vortex flowmeter having configurable terminations for coupling to a variety of pressure or differential pressure sensors or transmitters for advanced process fluid measurements or calculations.

61 Claims, 15 Drawing Sheets

U.S. PATENT DOCUMENTS

| | | | |
|---|---|---|---|
| 4,212,209 A * | 7/1980 | Newbold et al. | 73/721 |
| 4,270,391 A | 6/1981 | Herzl | 73/861.22 |
| 4,285,246 A | 8/1981 | Kita | 73/861.03 |
| 4,297,894 A | 11/1981 | Nagaishi et al. | 73/861.03 |
| 4,297,898 A | 11/1981 | Herzl | 73/861.22 |
| 4,339,661 A | 7/1982 | Pitt et al. | 250/227 |
| 4,372,169 A | 2/1983 | Hughes | 73/861.52 |
| 4,437,350 A | 3/1984 | Tamura et al. | 73/861.24 |
| 4,440,027 A | 4/1984 | Focht | 73/861.24 |
| 4,448,081 A | 5/1984 | Kolitsch et al. | 73/861.03 |
| 4,455,877 A | 6/1984 | Blechinger et al. | 73/861.22 |
| 4,459,847 A | 7/1984 | Kita | 73/861.22 |
| 4,476,728 A | 10/1984 | Otani | 73/861.22 |
| 4,523,477 A | 6/1985 | Miller | 73/81.02 |
| 4,545,258 A | 10/1985 | Coursolle | 73/861.22 |
| 4,561,310 A | 12/1985 | Barnard et al. | 73/861.02 |
| 4,589,279 A | 5/1986 | Mitsuyasu et al. | 73/118 |
| 4,605,315 A | 8/1986 | Kokoszka et al. | 374/144 |
| 4,630,484 A | 12/1986 | Mizuno et al. | 73/861.22 |
| 4,683,760 A | 8/1987 | Misumi | 73/861.22 |
| 4,730,500 A | 3/1988 | Hughes | 73/861.22 |
| 4,807,481 A | 2/1989 | Lew | 73/861.24 |
| 4,815,324 A | 3/1989 | Tada et al. | 73/861.22 |
| 4,827,430 A | 5/1989 | Aid et al. | 700/285 |
| 4,866,435 A | 9/1989 | Frick | 340/870.16 |
| 4,876,897 A | 10/1989 | DeCarlo et al. | 73/861.04 |
| 4,879,909 A | 11/1989 | Lew | 73/861.24 |
| 4,884,441 A | 12/1989 | Lew | 73/195 |
| 4,884,458 A | 12/1989 | Lew | 73/861.24 |
| 4,893,035 A | 1/1990 | Reynolds et al. | 307/520 |
| 4,896,541 A | 1/1990 | Hughes | 73/861.22 |
| 4,911,019 A | 3/1990 | Lew | 73/861.24 |
| 4,926,695 A | 5/1990 | Kleven et al. | 73/861.24 |
| 4,941,361 A | 7/1990 | Lew | 73/861.24 |
| 4,972,723 A | 11/1990 | Lew | 73/861.24 |
| 4,973,062 A | 11/1990 | Lew | 73/861.24 |
| 4,986,134 A | 1/1991 | Lew | 73/861.24 |
| 5,005,426 A | 4/1991 | Lew | 73/861.22 |
| 5,060,522 A | 10/1991 | Lew | 73/861.02 |
| 5,076,105 A | 12/1991 | Lew | 73/861.24 |
| 5,090,251 A | 2/1992 | Lew | 73/861.24 |
| 5,095,760 A | 3/1992 | Lew | 73/861.24 |
| 5,101,668 A | 4/1992 | Lew | 73/861.24 |
| 5,109,704 A | 5/1992 | Lew | 73/861.24 |
| 5,121,658 A | 6/1992 | Lew | 73/195 |
| 5,127,273 A | 7/1992 | Lew | 73/861.24 |
| 5,152,181 A | 10/1992 | Lew | 73/861.02 |
| 5,214,965 A | 6/1993 | Lew | 73/861.24 |
| 5,220,842 A | 6/1993 | Lew | 73/861.24 |
| 5,309,771 A | 5/1994 | Lew et al. | 73/861.22 |
| 5,351,556 A | 10/1994 | Lew et al. | 73/861.22 |
| 5,372,046 A | 12/1994 | Kleven et al. | 73/861.22 |
| 5,429,001 A | 7/1995 | Kleven | 73/861.22 |
| 5,435,188 A | 7/1995 | Lew et al. | 73/861.22 |
| 5,447,073 A | 9/1995 | Kalinoski | 73/861.24 |
| 5,463,904 A | 11/1995 | Kalinoski | 73/861.24 |
| 5,477,737 A | 12/1995 | Lew | 73/704 |
| 5,493,915 A | 2/1996 | Lew et al. | 73/861.24 |
| 5,495,769 A | 3/1996 | Broden et al. | 73/718 |
| 5,501,099 A | 3/1996 | Whorff | 73/29.01 |
| 5,503,021 A | 4/1996 | Lew | 73/661 |
| 5,808,209 A * | 9/1998 | Zielinska et al. | 73/861.22 |
| 5,913,247 A | 6/1999 | Steuer | 73/861.22 |
| 6,003,383 A | 12/1999 | Zielinski et al. | 73/861.22 |
| 6,101,885 A * | 8/2000 | Touzin et al. | 73/861.22 |
| 6,170,338 B1 | 1/2001 | Kleven et al. | 73/861.22 |
| 6,220,103 B1 | 4/2001 | Miller et al. | 73/861.22 |
| 6,317,051 B1 | 11/2001 | Cohen | 340/603 |
| 6,651,512 B1 * | 11/2003 | Kleven et al. | 73/861.22 |
| 6,752,027 B1 * | 6/2004 | Kalinoski | 73/861.22 |
| 6,843,139 B2 * | 1/2005 | Schumacher et al. | 73/861.52 |

FOREIGN PATENT DOCUMENTS

| | | |
|---|---|---|
| DE | 196 19 632 A1 | 11/1997 |
| DE | 102 40 189 A1 | 3/2004 |
| EP | 0549945 A2 | 7/1993 |
| EP | 0 666 468 A | 8/1995 |
| EP | 1 213 566 A2 | 6/2002 |
| JP | 3-277973 | 12/1991 |
| JP | 5-18798 | 1/1993 |
| WO | WO90/04230 | 4/1990 |

* cited by examiner

SIMPLIFIED FLUID PROPERTY MEASUREMENT

CROSS REFERENCE TO CO-PENDING APPLICATIONS

This application claims the priority of an earlier filed co-pending provisional patent application Ser. No. 60/556,399, filed Mar. 25, 2004, entitled "COMBINATION DP/MASS FLOWMETER".

BACKGROUND OF THE INVENTION

The present invention relates to industrial fluid flow measurement systems, and more particularly, to systems that provide a mass flow measurement or other fluid property measurements.

Mass flow of a fluid can be estimated using various techniques. For example, current differential pressure measurement techniques can be used as a basis for calculating mass flow. Generally, an obstruction device, such as an orifice plate, partially obstructs the fluid flow and generates a differential pressure between the upstream flow and the downstream flow. Measuring the differential pressure can provide an indication of flow. Generally, additional information is required in order for the differential pressure measurement to provide mass flow information. Specifically, information about the composition and temperature of the fluid must be known or measured. This is due, at least in part, to the fact that the differential pressure is not based only on the flow, but also on the fluid density, which itself may be a function of temperature. Further, the nature of the flow, laminar or turbulent, may affect the differential pressure reading.

Mass flow can also be calculated using a vortex flowmeter system as a basis. Vortex flowmeter systems are used in the industrial process control field for directly measuring the flow rate of a fluid through a conduit. Vortex flowmeters are typically inserted into the pipe or conduit that carries the fluid to be measured. Industry applications include petroleum, chemical, pulp and paper, mining and materials, oil and gas. The fluids to be measured are often hazardous and may be flammable or explosive. The fluids may also include condensate, deposits or other properties that can make flow measurements difficult. In these applications, safety and measurement accuracy are critical.

The operating principle of a vortex flowmeter is based on the phenomenon of vortex shedding known as the von Karman effect. As fluid passes a bluff body, it separates and generates small as eddies or vortices that are shed alternately along and behind each side of the bluff body. These vortices cause areas of fluctuating pressure that are detected by a sensor. The frequency of vortex generation is essentially proportional to fluid velocity.

Generally, vortex flowmeters provide a volumetric flow output. Quite simply, this volumetric flow output is the product of the fluid flow velocity (proportional to vortex frequency) through the conduit multiplied by the area of the conduit. Some vortex flowmeter systems are known that can provide mass flow output. Generally, such systems measure the temperature and absolute pressure of the fluid flowing from the conduit. Then, using some assumptions about the nature of the fluid and/or composition thereof, a calculation can be approximated for the mass flow of the fluid. Generally, this calculation is merely an approximation and can be susceptible to error when the composition changes. Moreover, the relative complexity of the calculations involved are difficult to provide continuously in a real-time manner.

Measuring mass flow of a fluid using both a differential pressure measurement and vortex measurement vastly simplifies the calculations and allows density and mass flow to be easily provided. Such an approach is described in United States Patent Publication US 2002/0096208 published Jul. 25, 2002. While the disclosure of that patent publication provides an effective starting point, much work remains to be done before such principles can be effectively incorporated into real-world implementations. For example, although the calculations themselves become simpler, the publication speaks of requiring two measurement devices: a differential pressure flow measuring element and a vortex flow measuring element are required. Accordingly, the real-world cost to an end user for such calculation simplicity is potentially double the equipment cost that is currently required. Systems that could provide the advantages of differential pressure and vortex measurement without the associated substantial cost increase would allow the industry to adopt such advantageous technology more readily.

SUMMARY OF THE INVENTION

A process fluid measurement system provides a first measurement relative to process fluid flowing in a pipe. An additional measurement of process fluid flow velocity in the pipe is combined with the first measurement to provide a simplified indication of mass fluid flow and/or density or other fluid parameter. In some embodiments, the first measurement is a differential pressure measurement. Additionally, one embodiment provides a vortex flowmeter having configurable terminations for coupling to a variety of pressure or differential pressure sensors or transmitters for advanced process fluid measurements or calculations.

DETAILED DESCRIPTION OF EMBODIMENTS

Embodiments of the present invention generally take advantage of certain synergies created by the combination of differential pressure flow measurement and vortex flow measurement. While embodiments of the present invention will be described with respect to differential pressure flow measurement in conjunction with vortex flow measurement, those skilled in the art will recognize that embodiments of the present invention can be practiced in any application where a first measurement relative to a process fluid can be combined with a direct reading of flow velocity. Accordingly, vortex flow measurement, described herein, is simply one example of fluid velocity measurement in accordance with embodiments of the present invention.

Figure 1:
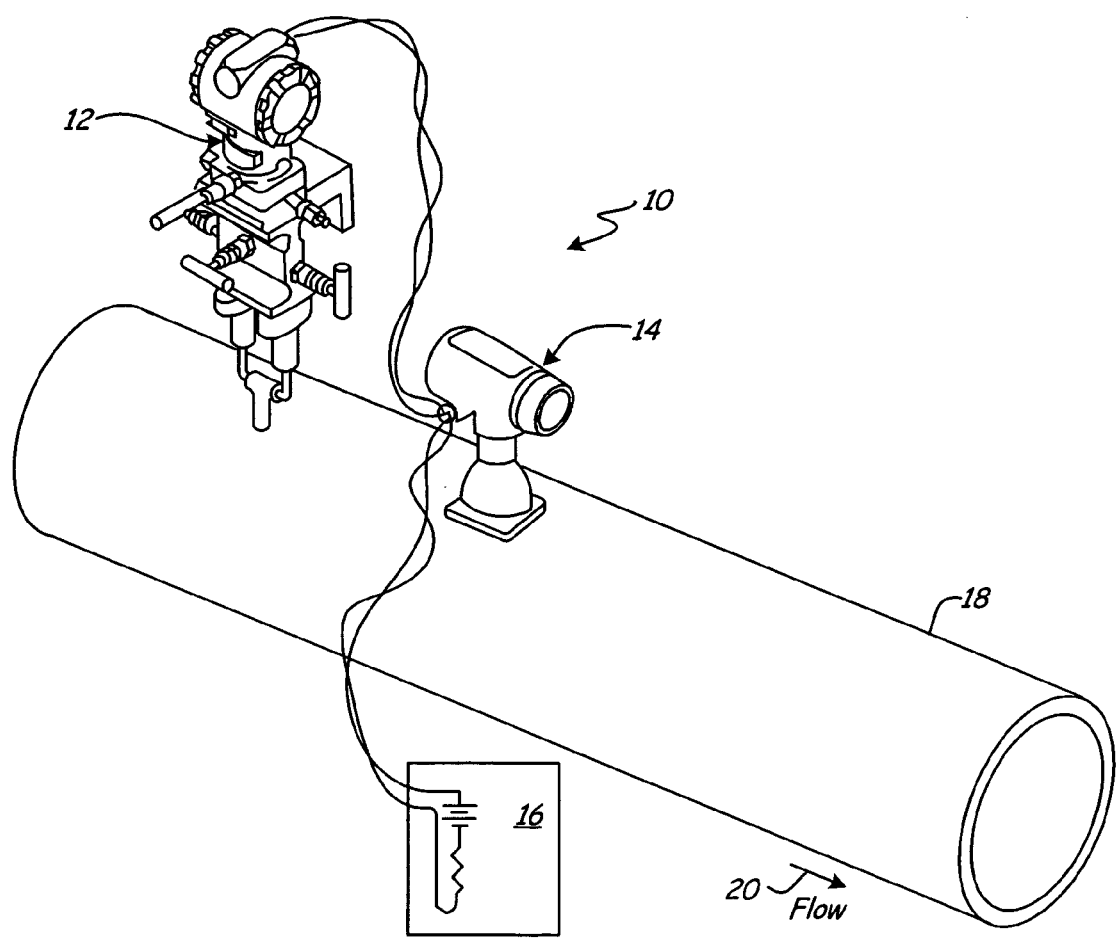
FIG. 1 is a diagrammatic view of a process fluid measurement system in accordance with an embodiment of the present invention.

FIG. 1 is a diagrammatic view of a fluid mass flow measurement system 10. System 10 includes differential pressure flow measurement system 12 and vortex flow measurement system 14, both of which are coupled to control room 16. For simplicity, control room 16 is simply modeled as a voltage source and resistance. Devices 12 and 14 are illustrated as being mounted diagrammatically to a process fluid pipe 18 having fluid flowing therein in the direction of arrow 20.

Differential pressure flow measurement device 12 can be any suitable device including, that sold under the trade designation 3051SFA Pro Bar Flowmeter available from Rosemount Inc. of Eden Prairie, Minn. Vortex flow measurement device 14 can also be any suitable device. In one embodiment, device 14 is that available under the trade designation 8800C from Rosemount Inc. Both devices 12 and 14 are considered field devices in that they are suitable for operation in generally inhospitable environments. Accordingly, devices 12 and 14 are able to withstand the extremes of outside temperature, vibrations associated with operation in the process industry, as well as EMI and RFI interference. Field devices 12 and 14 can generally communicate with one another and/or control room 16 over one of any suitable process industry standard communication protocols. Preferably, devices 12 and 14 communicate in accordance with the FOUNDATION™ Fieldbus protocol. The Fieldbus protocol is an all-digital protocol that is also able to power connected field devices. Accordingly, field wiring is substantially simplified when such a process industry standard communication protocol is employed.

Some embodiments of the present invention employ differential pressure measurement, in one form or another, to obtain flow information. This flow information is then supplemented with fluid velocity information that can be sensed in any suitable manner. The equations for differential pressure flow measurement are set forth below:

$$Q = C_{\Delta P} * \sqrt{\frac{\Delta P}{\rho}} \qquad \text{Eq. 1}$$

$$C_{\Delta P} = D^2 K \qquad \text{Eq. 2}$$

Q=volumetric flow rate (ft³/sec);

$C_{\Delta P}$=differential pressure flow calibration constant dependent upon pipe inner diameter (ID);

ΔP=differential pressure;

ρ=density (lbm/ft³);

D²=Inside Pipe Diameter squared (ft²); and

K=constant.

The vortex volumetric flow equations are as follows:

$$Q = C_v * f \qquad \text{Eq. 3}$$

$$C_v = \frac{d * A}{St} \qquad \text{Eq. 4}$$

f is the vortex shedding frequency (Hz);

d is the shedder bar probe (ft);

$C_v$ is the vortex meter calibration constant;

A=inside pipe area (ft²); and

St is the Strouhal number.

Multiplying the vortex volumetric flow rate Q by the fluid density provides a measure of mass flow. Combining the volumetric terms of differential pressure flow and vortex volumetric flow yields Equation 5:

$$C_v * f = C_{\Delta P} * \sqrt{\frac{\Delta P}{\rho}} \qquad \text{Eq. 5}$$

Solving the equations for density yields Equation 6:

$$\rho = \left(\frac{C_{\Delta P}}{C_v}\right)^2 * \frac{\Delta P}{f^2} \qquad \text{Eq. 6}$$

Finally, solving for mass flow (using the vortex equation) yields the following Equation 7:

$$\dot{m} = \left(\frac{C_{\Delta P}}{C_v}\right)^2 * \frac{\Delta P}{f^2} * C_v * f \qquad \text{Eq. 7}$$

which simplifies to Equation 8:

$$\dot{m} = \frac{C_{\Delta P}^2}{C_v} * \frac{\Delta P}{f} \qquad \text{Eq. 8}$$

Figure 2:
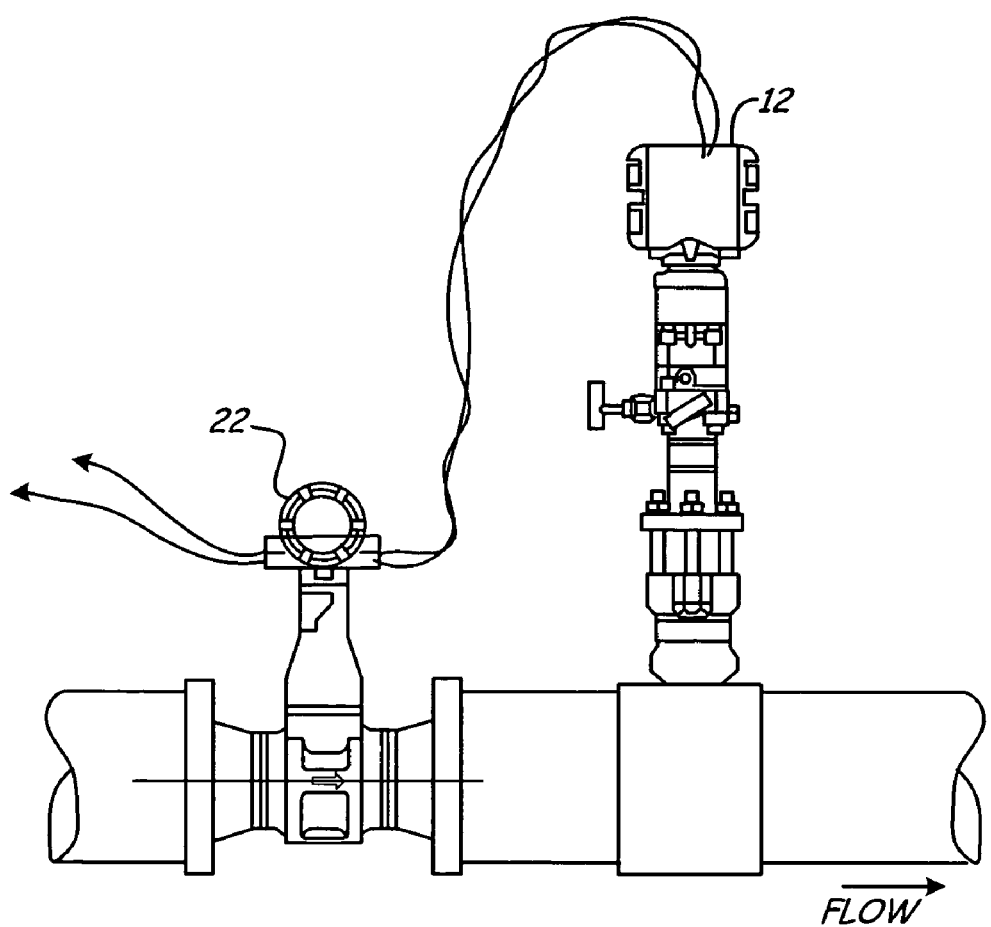
FIG. 2 is a diagrammatic view of a process fluid measurement system in accordance with another embodiment of the present invention.

FIG. 2 illustrates another arrangement where vortex flowmeter 22 is used in conjunction with a differential pressure flow measurement device 12. FIG. 2 illustrates that the vortex flow measurement device 22 can be disposed upstream from the differential pressure flow measurement device. Additionally, since the two field devices are coupled together, the provision of a mass flow rate and/or a density calculation can be done by fluid flow circuitry, such as a microprocessor, in either, or both of the field devices. However, it is also contemplated that each field device may simply report its measured information, and the ultimate calculation of mass flow and/or density could be done remotely, such as by a controller in control room 16.

FIGS. 3A-3E illustrate various ways in which a vortex flow transmitter can be coupled to receive additional sensor information. In the various embodiments illustrated in FIGS.

3A-3E, a plurality of configurable terminations 41A-41D are illustrated coupling various types of sensors and/or sensing systems to the vortex sensing field device. Although four such configurable terminations are illustrated, any suitable number may be used. Additionally, while a switch 52 is shown coupling the terminations 41A-41D to analog-to-digital converter 50, any suitable component can be used to allow the microprocessor to selectable couple certain terminations 41A-41D to converter 50.

Figure 3A:
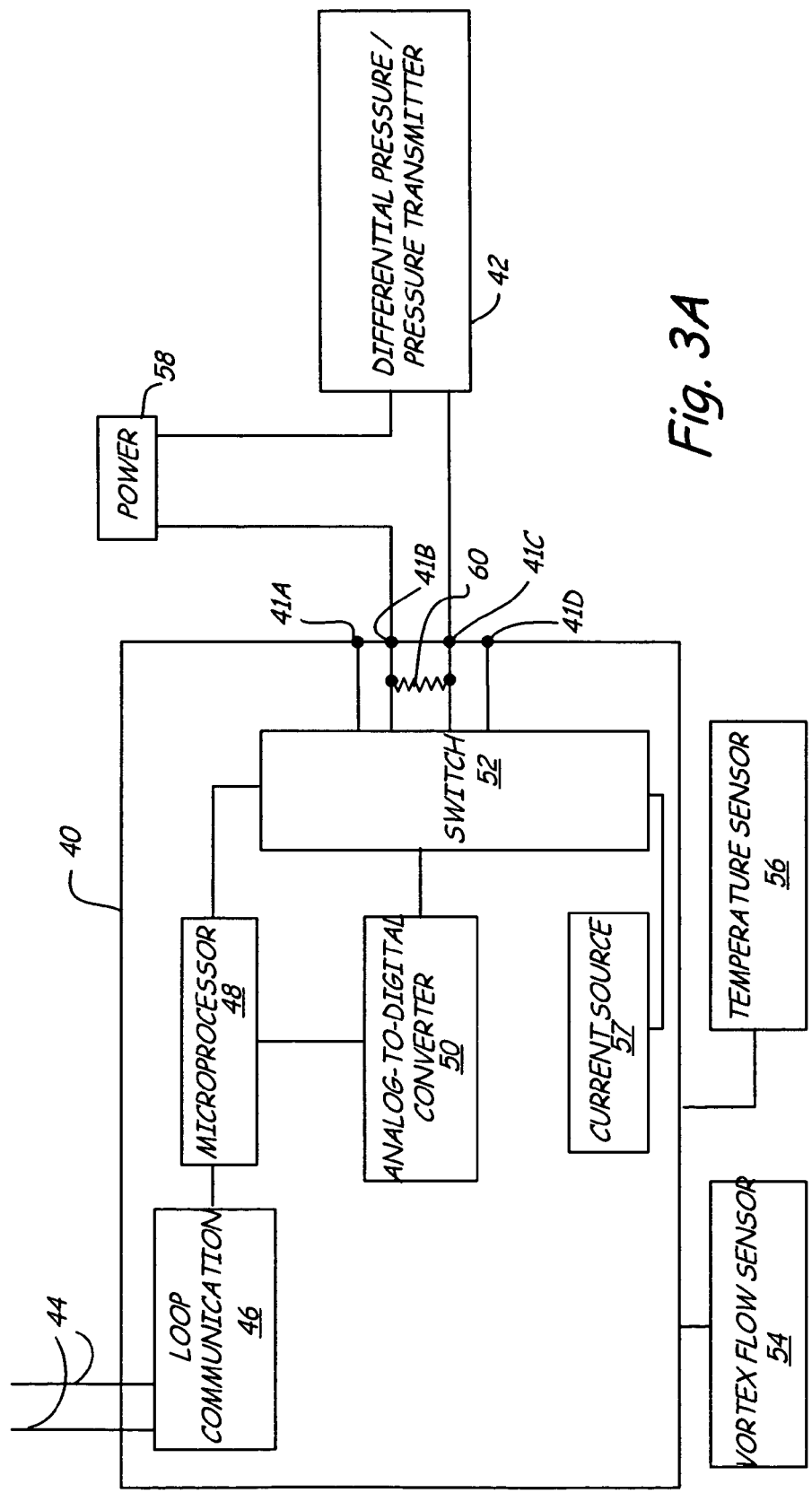
FIGS. 3A-3E are block diagrams illustrating various ways that a vortex sensing field device can receive information in accordance with embodiments of the present invention.

FIG. 3A is a diagrammatic illustration of a representative vortex flowmeter 40 coupled to a differential pressure or pressure transmitter 42 using terminations 41B and 41C. In this embodiment, terminations 41A and 41D are not used. Embodiments of the present invention include vortex flowmeter 40 coupled to any additional sensor or field device to receive additional process fluid information which can be combined with the fluid velocity measurement to provide higher level flow parameters such as mass fluid flow. Vortex flowmeter 40 is adapted to couple to process communication loop 44 via loop communication module 46. Loop communication module 46 allows flowmeter 40 to communicate upon a process communication loop in accordance with a process industry standard protocol such as, but not limited to, FOUNDATION™ Fieldbus, HART®, Profibus-PA, Modbus, Controller Area Network (CAN) or others. Module 46 is coupled to microprocessor 48, which is further coupled to analog-to-digital converter 50 and switch 52.

Microprocessor 48 controls switch 52 such that analog-to-digital converter 50 can provide digital information relative to process variable transmitter 42. Transmitter 42 can, for example, measure fluid pressure (absolute or gage) or differential pressure. Microprocessor 48 suitably actuates switch 52 in order to selectively couple one of certain configurable terminations 41A, 41B, 41C and 41D to converter 50, thus allowing for a configurable interface based upon a selection made by microprocessor 48 so the vortex flowmeter can receive additional information relative to the process fluid from another sensor. Current source 57 can be used in situations where a current must be driven through a resistance in order to measure a voltage relative to transmitter 42.

While generally temperature information is not required when flow is sensed with differential pressure and vortex methods, the knowledge of fluid temperature can facilitate providing higher level flow parameters such as heat content, heat flow, fluid quality and/or composition. Vortex flow sensor 54 and temperature sensor 56 may be coupled to the microprocessor 48 of vortex flowmeter 40 in any suitable manner as is known in the art to provide flow and temperature parameter information to the flowmeter. Transmitter 42, may be coupled to power supply 58 and controls current flowing therethrough based upon a parameter of interest, such as differential pressure, relative to the fluid. The current controlled by transmitter 42 is converted to a voltage by a virtue of resistor 60. Accordingly, microprocessor 48 can use analog-to-digital converter 50 and switch 52 to measure an additional parameter of interest via transmitter 42.

Figure 3B:
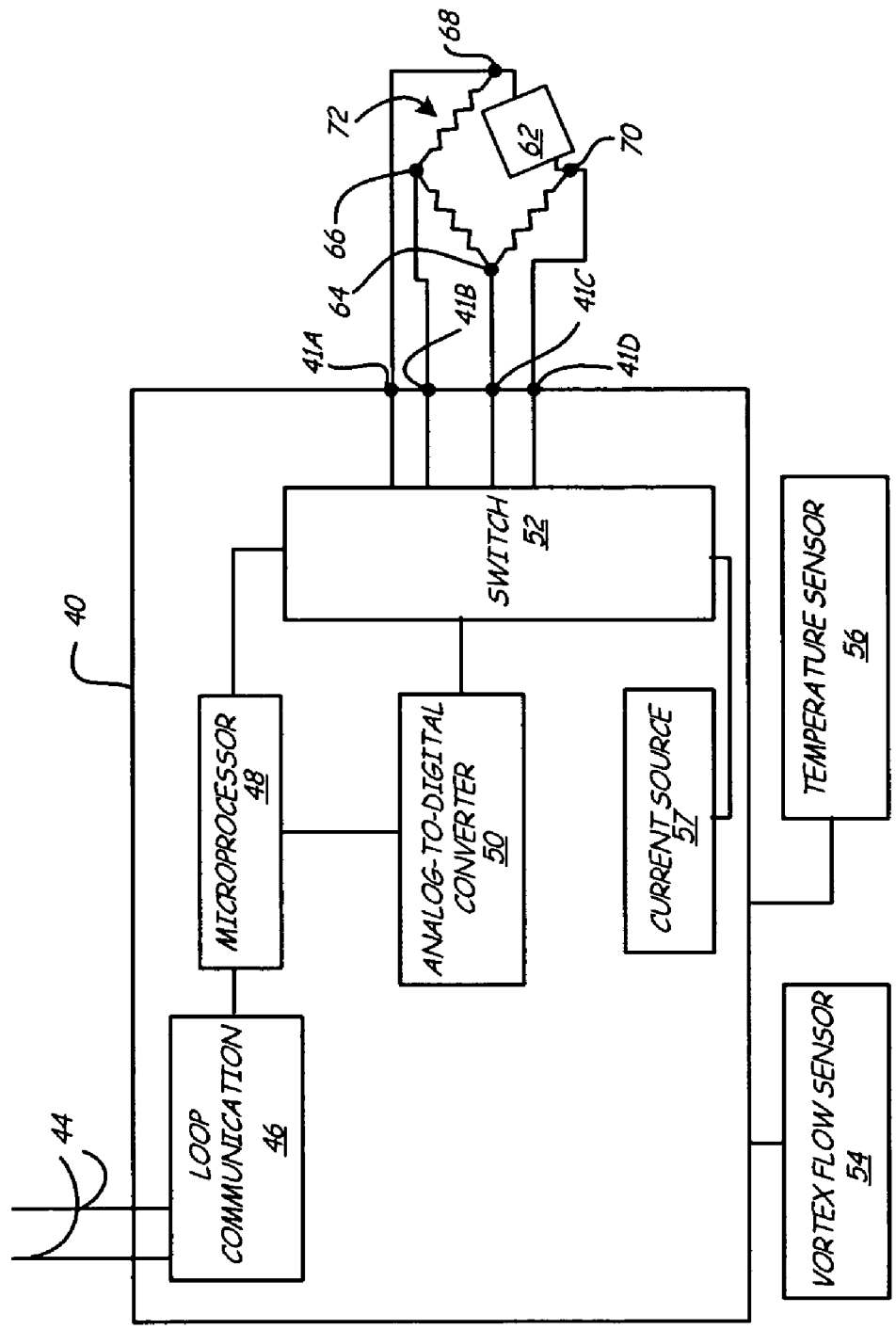

FIG. 3B is a diagrammatic view of vortex flowmeter 40 coupled to a piezoresistive pressure sensor 62 using all of configurable terminations 41A, 41B, 41C and 41D. Many components of flowmeter 40 are similar to that set forth with respect to FIG. 3A, and like components are numbered similarly. FIG. 3B illustrates switch 52 coupled to four different nodes 64, 66, 68 and 70 of bridge 72. Piezoresistive pressure transducer 62 is disposed within bridge 72 between nodes 68 and 70. Suitable energization of current source 57 through switch 52 can drive the bridge 72 in such a way that microprocessor 48 is able to obtain an extremely accurate indication of the resistance of the piezoresistive pressure transducer. The piezoresistive pressure transducer provides an indication of pressure with respect to the fluid flow.

Figure 3C:
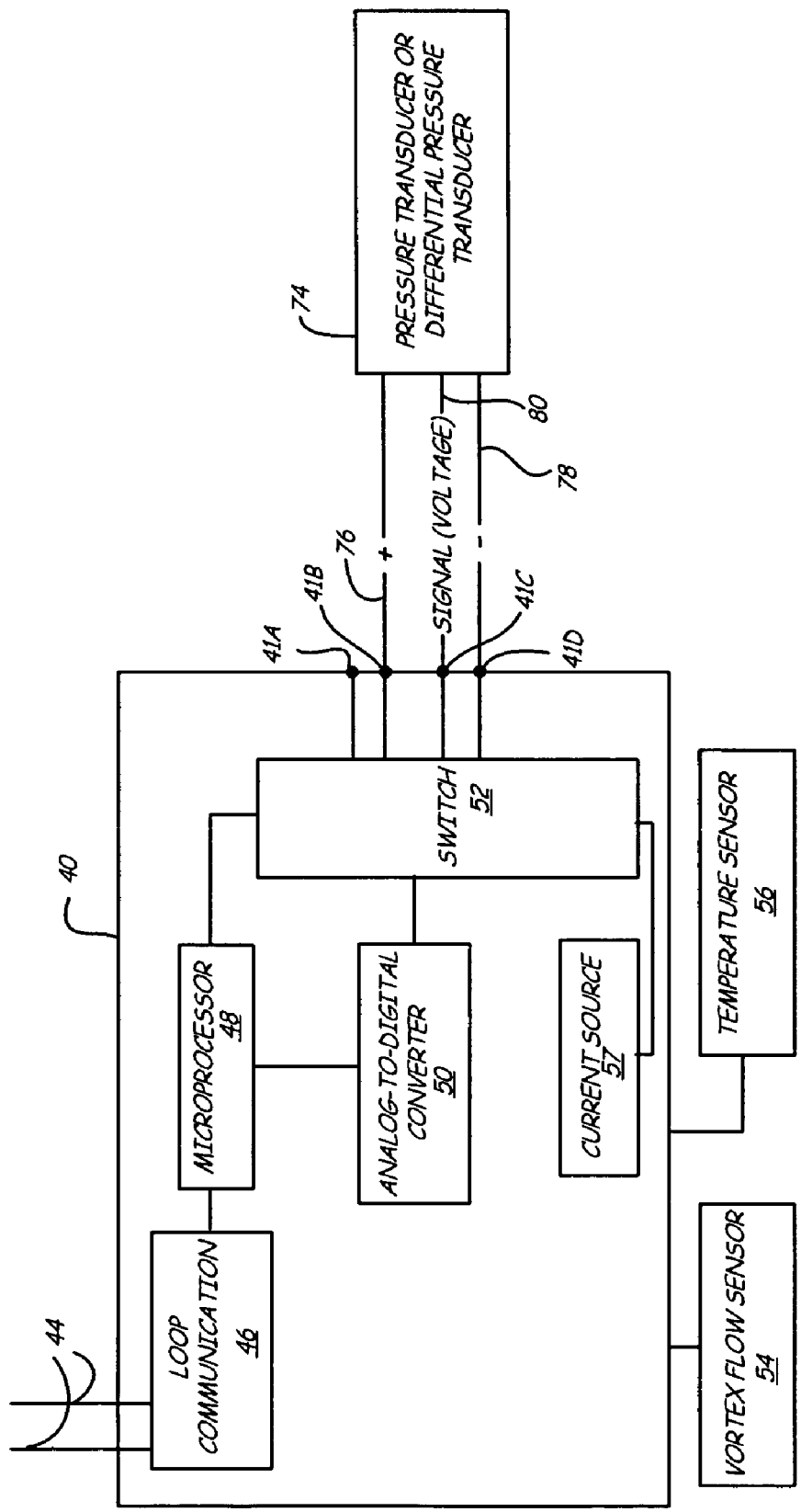

FIG. 3C is a diagrammatic view of vortex flowmeter 40 coupled to pressure transducer or differential pressure transducer 74 using configurable terminations 41B, 41C and 41D. The primary difference between FIG. 3C and the preceding figures is the manner in which switch 52 is coupled to transducer 74. Specifically, switch 52 wholly powers transducer 74 via positive and negative power lines 76 and 78 coupled to configurable terminations 41B and 41D, respectively. Communication between flowmeter 40 and pressure transducer 74 is done over signal line 80, coupled to termination 41C, in accordance with any suitable known method. Transducer 74 can be any suitable device that can operate upon the power supplied over lines 76 and 78 and provide an electrical indication over line 80 relative to a parameter of interest with respect to the fluid flow.

Figure 3D:
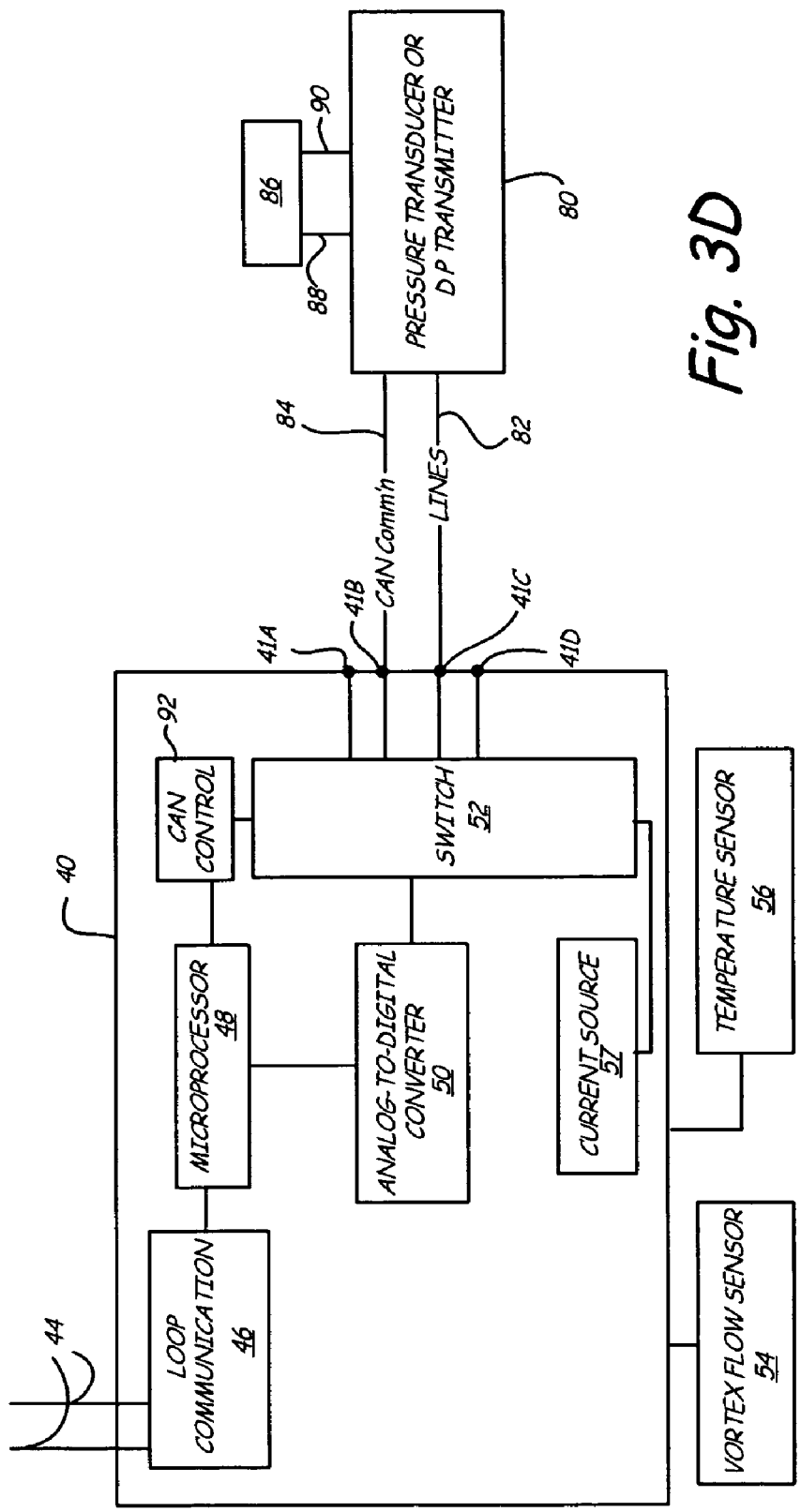

FIG. 3D is a diagrammatic view of vortex flowmeter 40 coupled to pressure transmitter or differential pressure transmitter 80 via lines 82, 84 coupled to terminations 41C and 41B, respectively. In embodiments where operating power for transmitter 80 is not provided over lines 82 and 84, transmitter 80 is also preferably coupled to a power supply 86 via lines 88, 90. In the embodiment illustrated in FIG. 3D, vortex flowmeter 40 includes Controller Area Network (CAN) control module 92 coupling microprocessor 48 to switch 52. CAN control module 92 allows microprocessor 48 to communicate over lines 82 and 84 with pressure transmitter 80 in accordance with the known Controller Area Network process communication protocol to receive an indication of for example, pressure or differential pressure from transmitter 80.

Figure 3E:
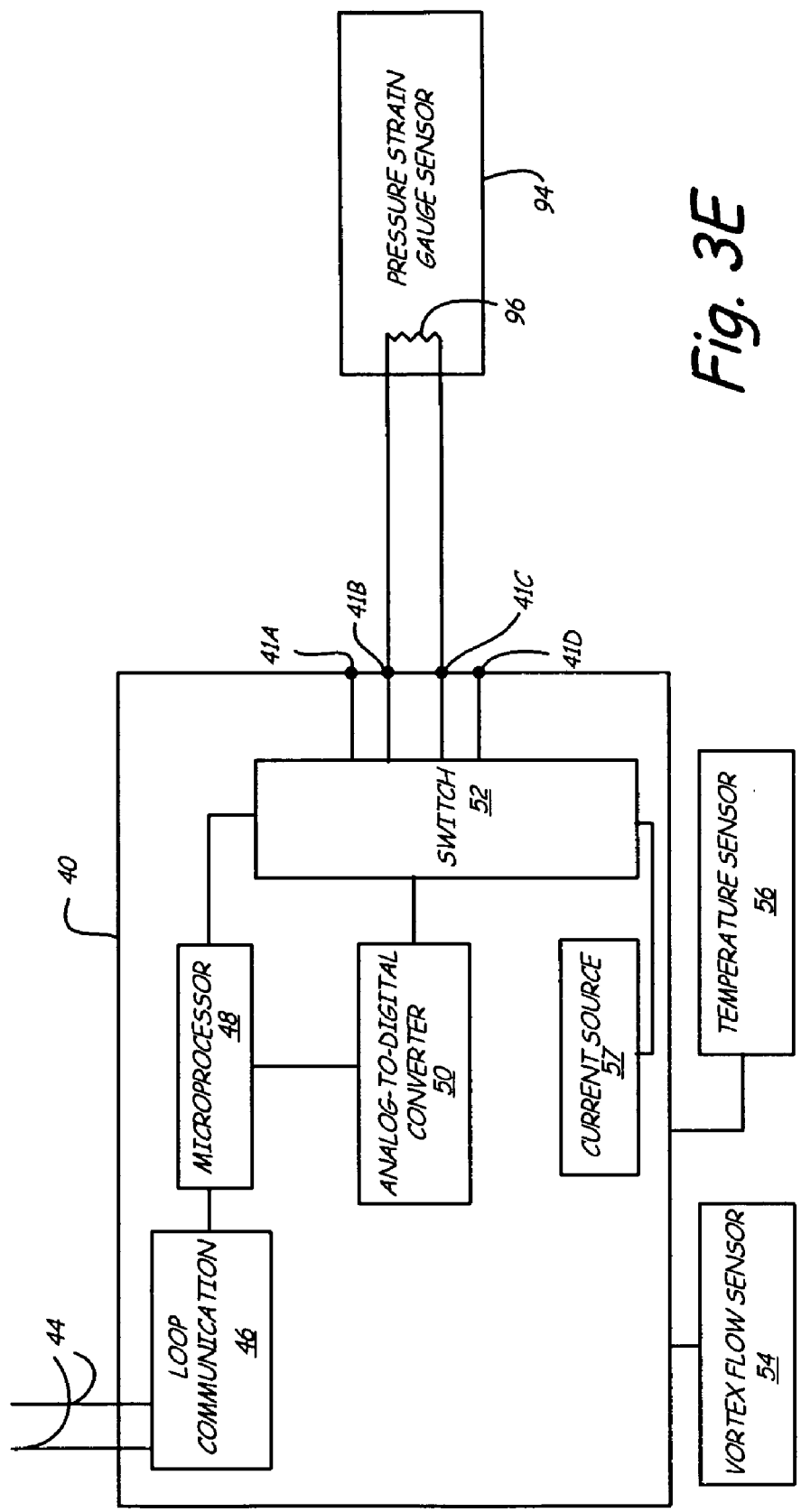

FIG. 3E is a diagrammatic view of vortex flowmeter 40 coupled to pressure strain gauge sensor 94 through terminations 41B and 41C. Switch 52 is coupled to pressure strain gauge sensor 94, which includes a resistance 96 that varies in response to strain. The measured strain is coupled to a member that deflects in response to pressure of the fluid. Accordingly, microprocessor 48 can measure the pressure of the fluid by determining the resistance of resistor 96. It is appreciated that these examples shown in FIGS. 3A-E illustrate the flexibility of having a vortex flowmeter 40 with configurable terminations (41A-D) which allows the flowmeter to couple to a variety of pressure or differential pressure sensors or transmitters and receive the process fluid information and perform additional calculations based on the additional information combined with the vortex fluid velocity information. In this way, a user can couple a variety of different types of pressure or differential pressure sensors or transmitters to the vortex flowmeter for added functionality.

Thus far, embodiments of the present invention have generally focused on the cooperation of a pair of field devices to provide a direct indication of fluid density and/or mass flow. However, the manner in which differential pressure and vortex sensing are done creates synergies that can be advantageously employed in accordance with embodiments of the present invention. Synergistic combinations are set forth below.

Figure 4:
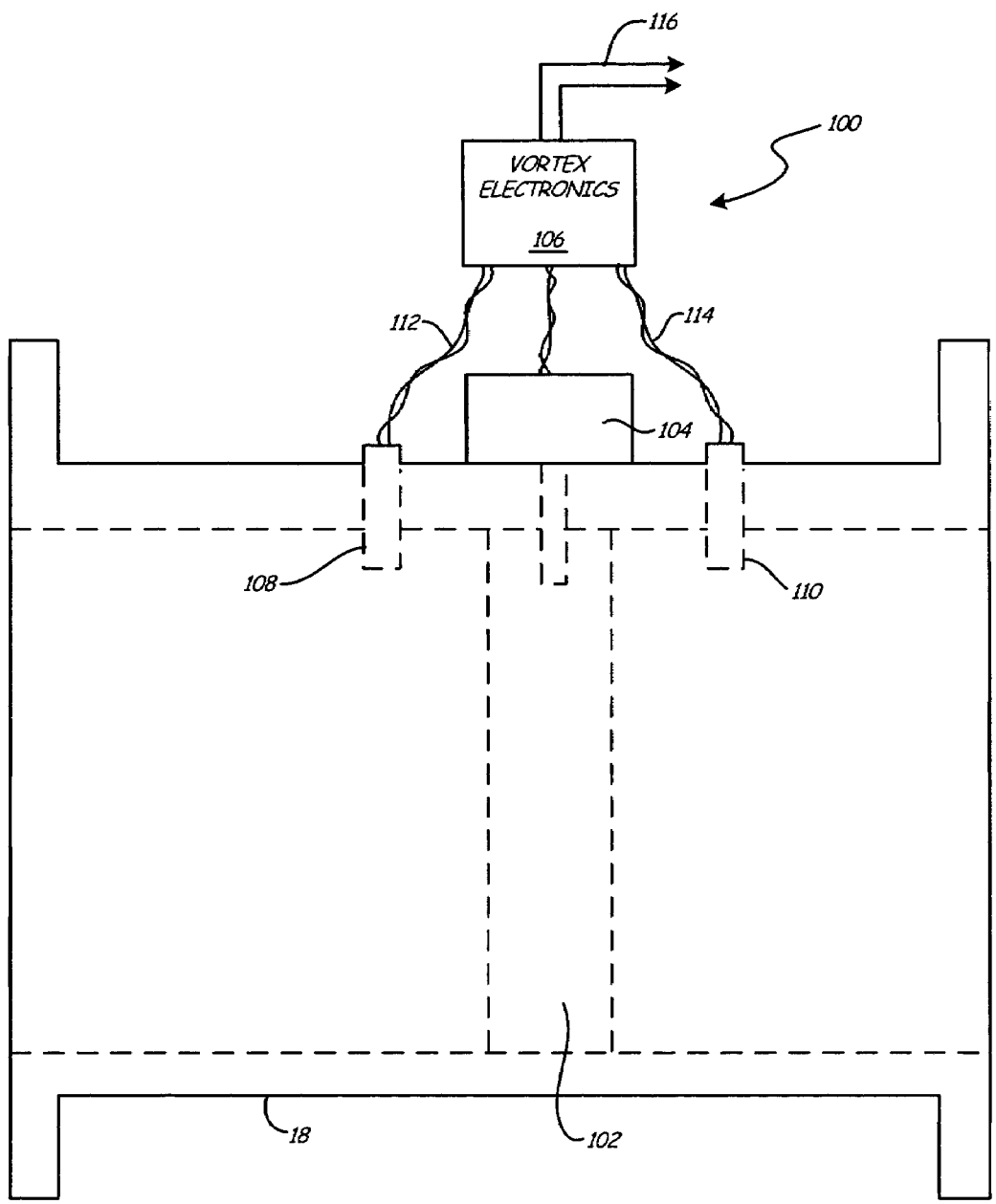
FIG. 4 is a diagrammatic view of a field device for measuring process fluid flow in accordance with an embodiment of the present invention.

FIG. 4 is a diagrammatic view of a vortex flowmeter 100 in accordance with an embodiment of the present invention. Vortex flowmeter 100 includes a vortex displaceable member 102 coupled to displacement sensor 104 which generates signals indicative of displacement, and thus vortices, to vortex electronics 106. The operation of vortex displaceable member 102, vortex sensor 104 and electronics 106 can be in accordance with any suitable known vortex sensing methods or techniques. One example of such a method is set forth in U.S. Pat. No. 4,926,695, assigned to Rosemount Inc., which provides a rocking beam vortex sensor. The aspect of system 100 in FIG. 4 that is inventive, is the combination of the known vortex sensing with pressure sensors 108 and 110. Specifically, fluid flow through pipe 18 will generate a differential pressure as it flows past vortex displaceable member 102. Thus, in this embodiment, vortex deflectable member 102 itself is being used as a fluid flow obstruction that generates differential pressure. The differential pressure is sensed by electronics 106 via connections 112 and 114. Thus, electronics 106 is able to perform a differential pressure measurement using pressure sensors 108 and 110, as well as a fluid velocity measurement using vortex sensing. The resultant mass flow and/or fluid density, as well as and other suitable properties, can be conveyed over process communication loop 116.

Each of pressure sensors 108, 110 is preferably a semiconductor-based pressure sensor. These types of pressure sensors are taught in U.S. Pat. No. 5,637,802, assigned to the Assignee of the present invention. Such semiconductor based pressure sensors generally provide a capacitance that varies with deflection of a portion of the semiconductor sensor. The deflection is in response to an applied pressure. The use of semiconductors, and in particular, sapphire provides a number of advantages. Sapphire is an example of a single-crystal material that when properly fusion-bonded has no material interface between the two bonded portions. Thus, the resulting structure is exceptionally robust. Additionally, semiconductor based sensors have extremely hysteresis and have an extremely high frequency response. Additional information related to semiconductor based pressure sensors can be found in U.S. Pat. Nos. 6,079,276; 6,082,199; 6,089,907; 6,484,585; and 6,520,020, all of which are assigned to the assignee of the present invention.

The use of a sapphire-based sensor is particularly beneficial in embodiments, such as that illustrated in FIG. 4, where the pressure sensor itself is exposed to the process fluid. Sapphire is corrosion resistant. Additionally, the sapphire pressure sensor has a fast response time, typically above 100 kHz, a feature that is particularly advantageous in embodiments of the present invention (such as described later with respect to FIG. 5) where the pressure sensor is also used to sense vortices. By directly placing the pressure sensor in contact with the process fluid, there is no isolation fluid, such as silicone oil, that can delay the pressure sensor response and/or dampen system effectiveness.

Transducer circuits currently used with semiconductor based pressure sensors provide very high accuracy and a fast response time. Additionally, many circuits can be combined on an application-specific integrated circuit (ASIC).

Figure 5:
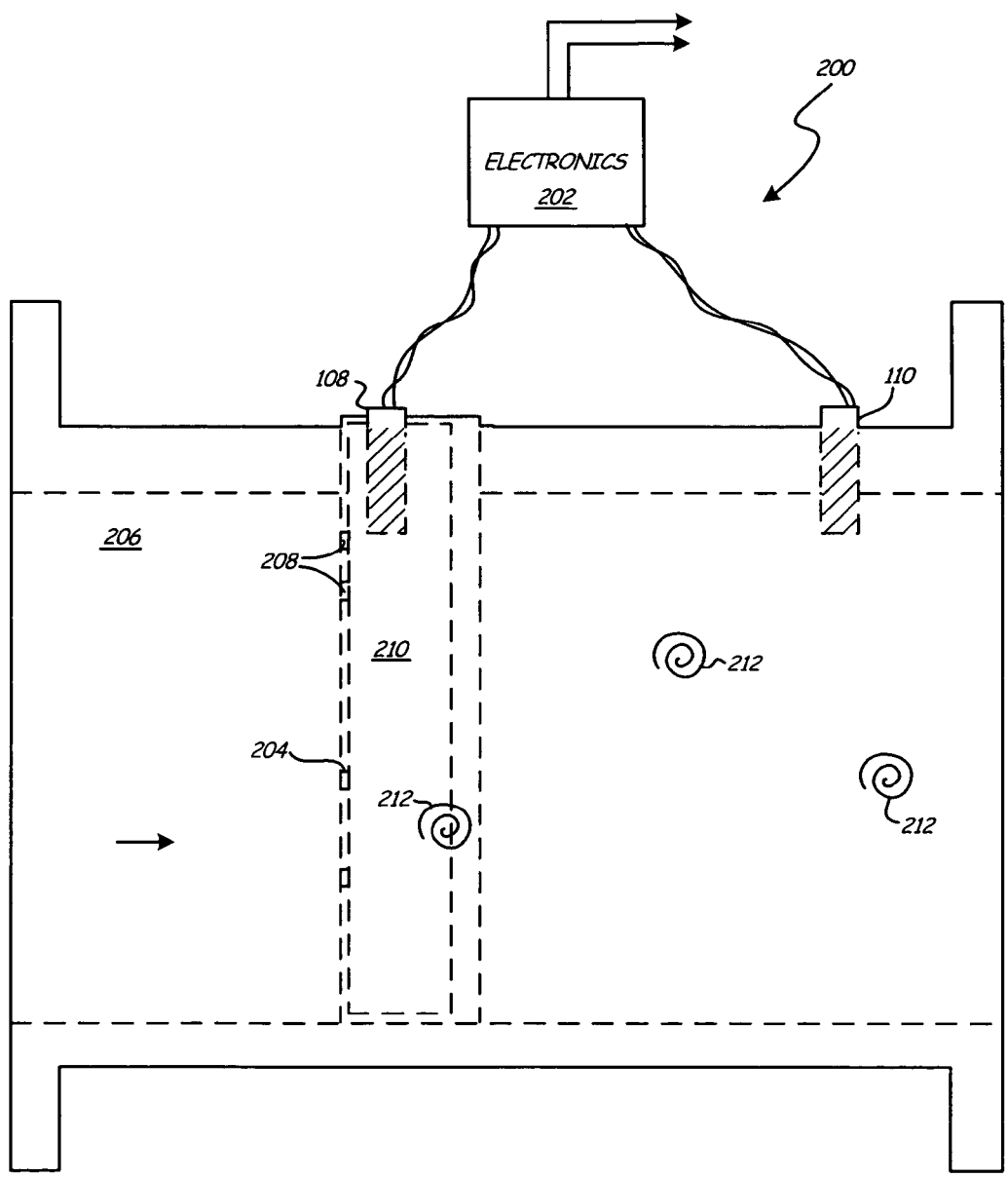
FIG. 5 is a diagrammatic view of another field device for measuring process fluid flow in accordance with another embodiment of the present invention.

FIG. 5 is a diagrammatic view of system 200 in accordance with an embodiment of the present invention. System 200 includes electronics module 202 coupled to a pair of pressure transducers 108 and 110. Pressure transducer 108 is disposed in dual-function primary element 204. Device 204 is dual function in that it couples pressure sensor 108 to upstream pressure 206 via holes 208, as well as generating vortices 212. Dual function element 204 is shaped to induce vortices 212 as fluid flows by element 204. Pressure sensor 110 is disposed downstream of element 204 and thus not only senses downstream pressure, but senses pressure fluctuations indicative of vortices 212 passing thereby.

Each of pressure sensors 108 and 110 is preferably a semiconductor-based pressure sensor. As set forth above, such sensors typically have a advantageous high-frequency response. Thus, sensor 110 is able to provide an indication of instantaneous pressure so rapidly, that pressure fluctuations indicative of vortices can be measured and/or detected.

Figure 6:
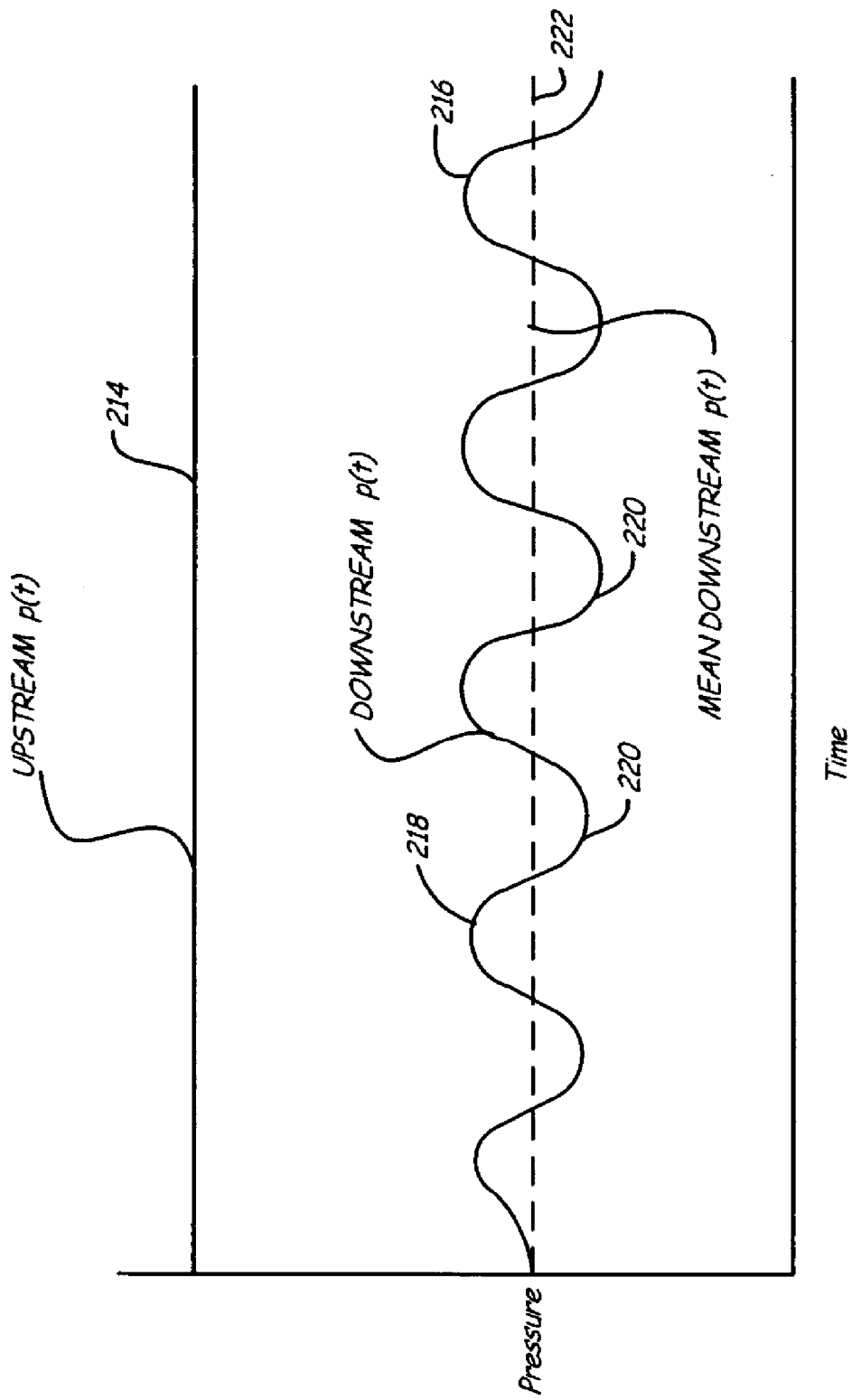
FIG. 6 is a chart of pressure versus time illustrating the use of a pressure sensor for detecting vortices and for determining differential pressure.

FIG. 6 is a diagram illustrating operation of system 200. Line 214 is indicative of a pressure measurement indication from pressure sensor 108 relative to upstream pressure over time. As illustrated in FIG. 6, the upstream pressure indicated by sensor 106 is relatively flat. In distinct contrast, pressure sensor 110 provides an indication of pressure illustrated at line 216. Line 216 includes a number of peaks 218 and valleys 220 indicative of local pressure increases and decreases proximate sensor 110 as vortices 212 pass by. An average 222 of the downstream pressure sensor 110 signal is useful for computing differential pressure. Accordingly, a differential pressure measurement can be obtained by subtracting average 222 from upstream pressure 214. Further, an indication of vortex frequency is provided by measuring the relative time between local peaks 218 and/or local valleys 220.

Figure 7:
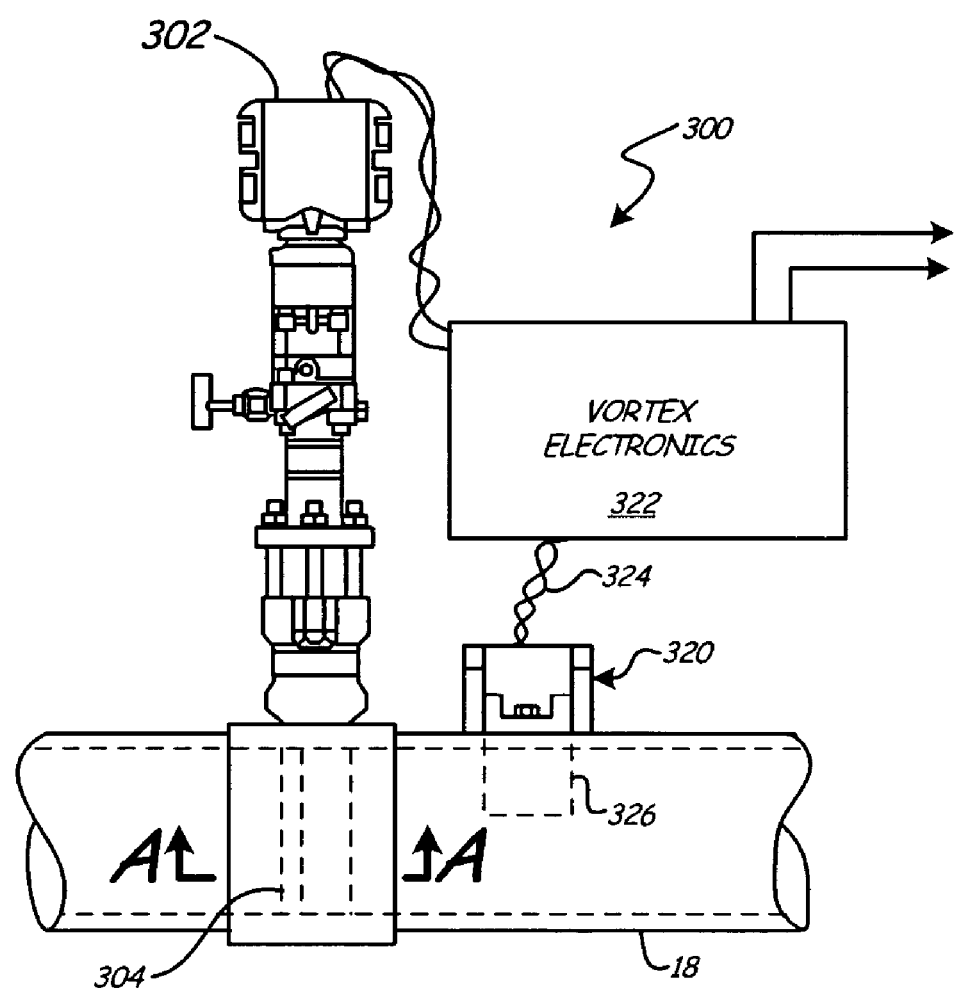
FIG. 7 is a diagrammatic view of a system for measuring process fluid flow in accordance with an embodiment of the present invention.
Figure 8:
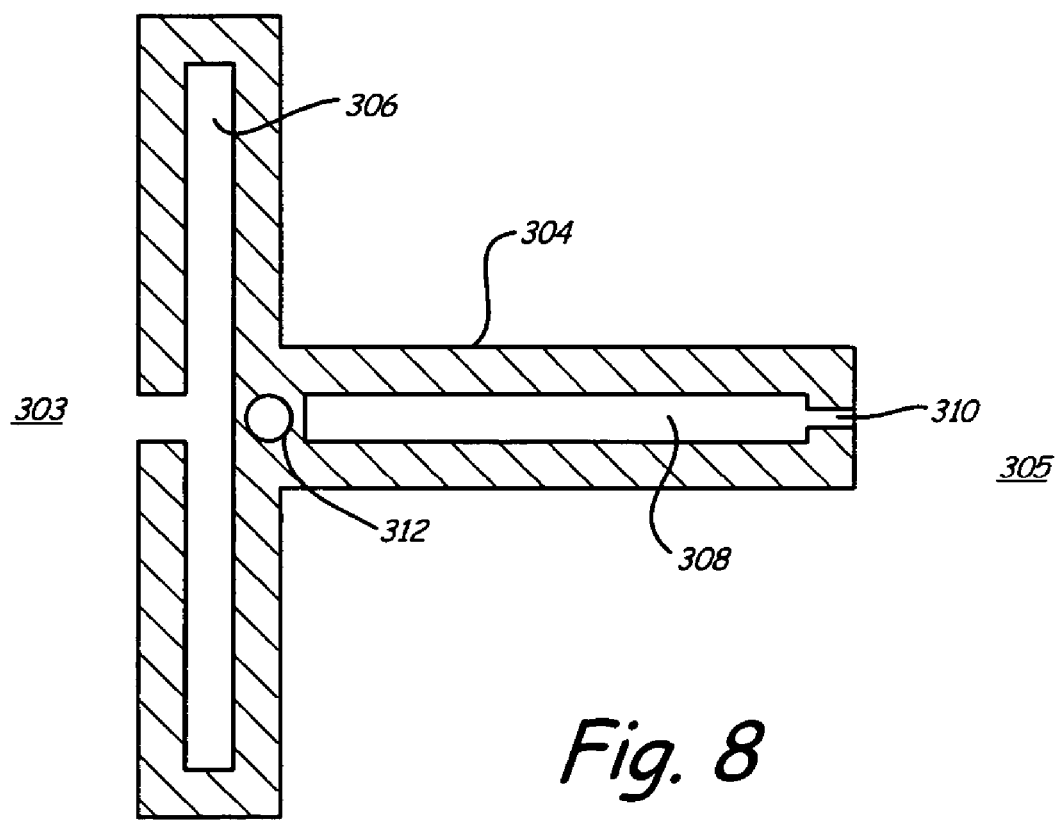
FIG. 8 is a cross section view of a dual-purpose primary element useful for embodiments of the present invention.

FIG. 7 is a diagrammatic view of a system 300 in accordance with another embodiment of the present invention. System 300 also employs a synergy between vortex sensing and differential pressure flow measurement. In particular, system 300 includes a differential pressure flow measurement device 302 which provides an indication of differential pressure relative to fluid flowing past element 304. Preferably, differential pressure flow measurement device 302 is in accordance with U.S. Pat. No. 6,470,755. Additionally, element 304 is preferably "T"-shaped, with the cross section across lines A-A being illustrated in FIG. 8. Other suitable shapes may be used as will be apparent. Element 304 couples first pressure 303 to chamber 306 and ultimately to an upstream pressure sensor in fluid communication with chamber 306. The upstream pressure sensor is preferably a semiconductor based pressure sensor. Second chamber 308 is coupled to a downstream pressure 305 via one or more holes 310. Additionally, element 304 may contain a recess or bore 312 that is suitable for inserting a temperature sensing device. The primary element shape(s) taught in U.S. Pat. No. 6,470,755, and as well as that set forth in FIGS. 7 and 8 provide an important feature. Specifically, the primary element while effectively transducing differential pressure, also generates Karman vortices downstream. As illustrated in FIG. 7, a vortex transducer 320 located downstream from primary element 304 provides an indication of vortices to vortex electronics 322 via lines 324.

In accordance with one aspect of the present invention, vortex transducer 320 is insertable in and anchored on a single side of pipe 18. Transducer 320 contains element 326 that is deflectable by passing vortices.

Figure 9A:
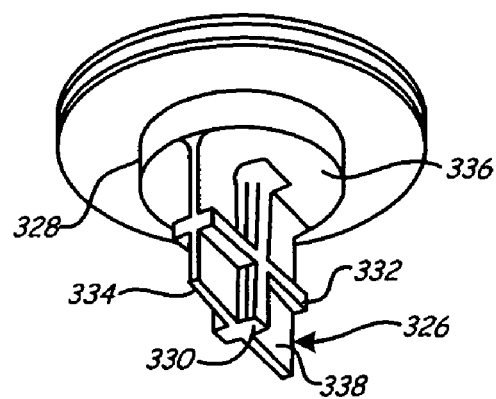
FIGS. 9A-9C are perspective, front elevation, and cross section views, respectively, of a vortex displaceable member in accordance with an embodiment of the present invention.
Figure 9B:
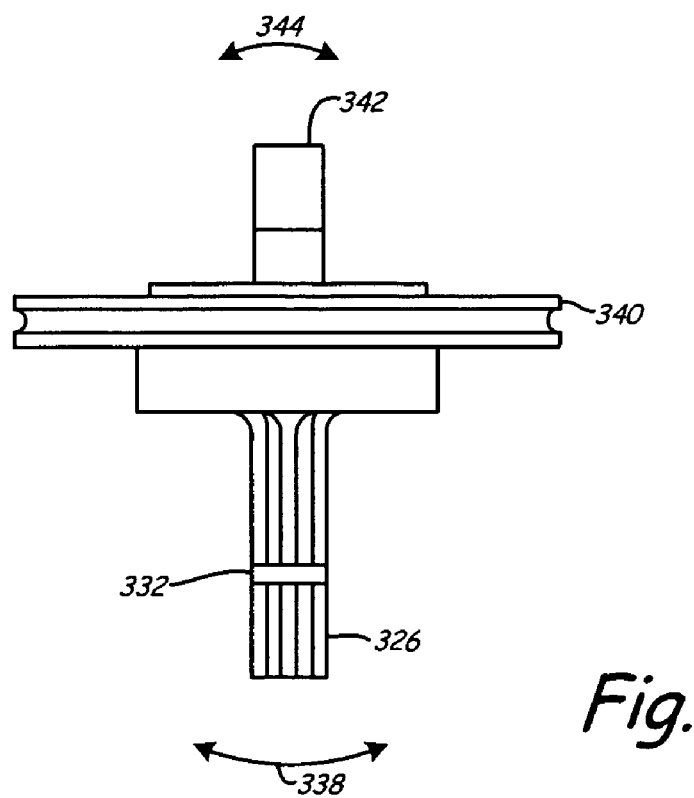
Figure 9C:
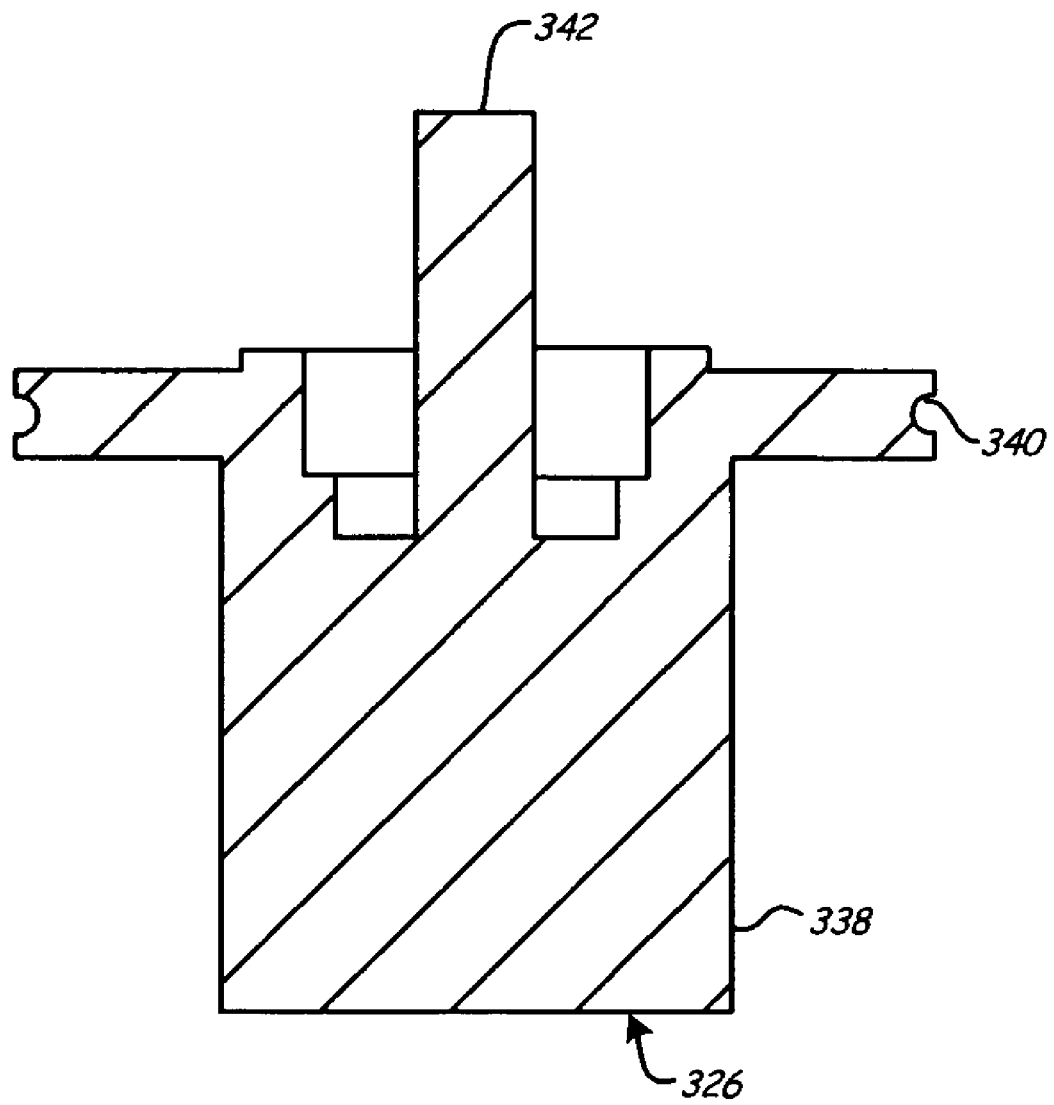

FIGS. 9A-9C illustrate element 326 of FIG. 7 is greater detail. Element 326 is configured to extend through a hole, sized to pass outer diameter 328, in pipe 18. Element 326 preferably includes a longitudinal beam 330 that is intersected by a transverse beam 332. A thinned displacement member 334 extends from surface 336 and provides lateral surface area 338. Lateral surface area 338, supported by longitudinal beam 330 and transverse beam 332, provides a surface against which the pressure of passing vortices act. As vortices pass, element 326 is displaced slightly in the directions of arrow 338. Since element 326 is preferably anchored at flange 340 the tip 342 will oscillate in a direction 344 opposite direction 338. Tip 342 is preferably coupled to a standard piezoelectric vortex flow sensing apparatus, such as that commercially available from Rosemount Inc. under part number 08800-0250-0001. Element 326 is a relatively low cost item since it can be easily fabricated using known casting techniques.

In operation, systems operating in accordance with embodiments of the present invention can provide quick and accurate indications of mass flow and/or density. The calculation of mass flow and/or density can be performed by a field device, or remotely. One way that the calculation can be performed remotely, is to create a function block in a digital communications environment such as that sold under the trade designation Plantweb® available from Fisher-Rosemount Systems Incorporated of Austin, Tex., to calculate mass flow and/or density from two standard flow measurements (one differential pressure flow, and one fluid velocity indication). In such a configuration, the calculation of mass flow and density is added to a function block. Essentially, the two measurements are then used to create a virtual densitometer and/or a virtual mass flowmeter. Any volumetric technology, including vortex, magnetic, turbine, positive displacement and ultrasonic can be used in combination with the differential pressure flow device to provide a fluid velocity indication.

As set forth above, embodiments of the present invention employ differential pressure measurement element. One preferred manner in which differential pressure is measured, is using the commercially available 485 Annubar® sensor from Rosemount Inc. This is preferred since the flow coefficient (K) is linear with flow. If an orifice plate is used, matters become somewhat more complicated since the discharge coefficient is then dependent upon the Reynold's number. A conditioning plate could be used in conjunction with the orifice plate in order to reduce the amount of straight run pipe.

The measurement of fluid temperature provides valuable information in some embodiments. Particularly, in a vortex measurement system that contains electronics for reading a vortex shedding signal from a piezo sensor, a temperature from a temperature sensor (such as a Resistance Temperature Device (RTD), thermocouple, etc.) and a differential pressure from a differential pressure sensor, mass flow can then be computed directly in the field device and $C_P$ can be compensated for sensitivity to process temperature and velocity, or Reynolds number.

Figure 10:
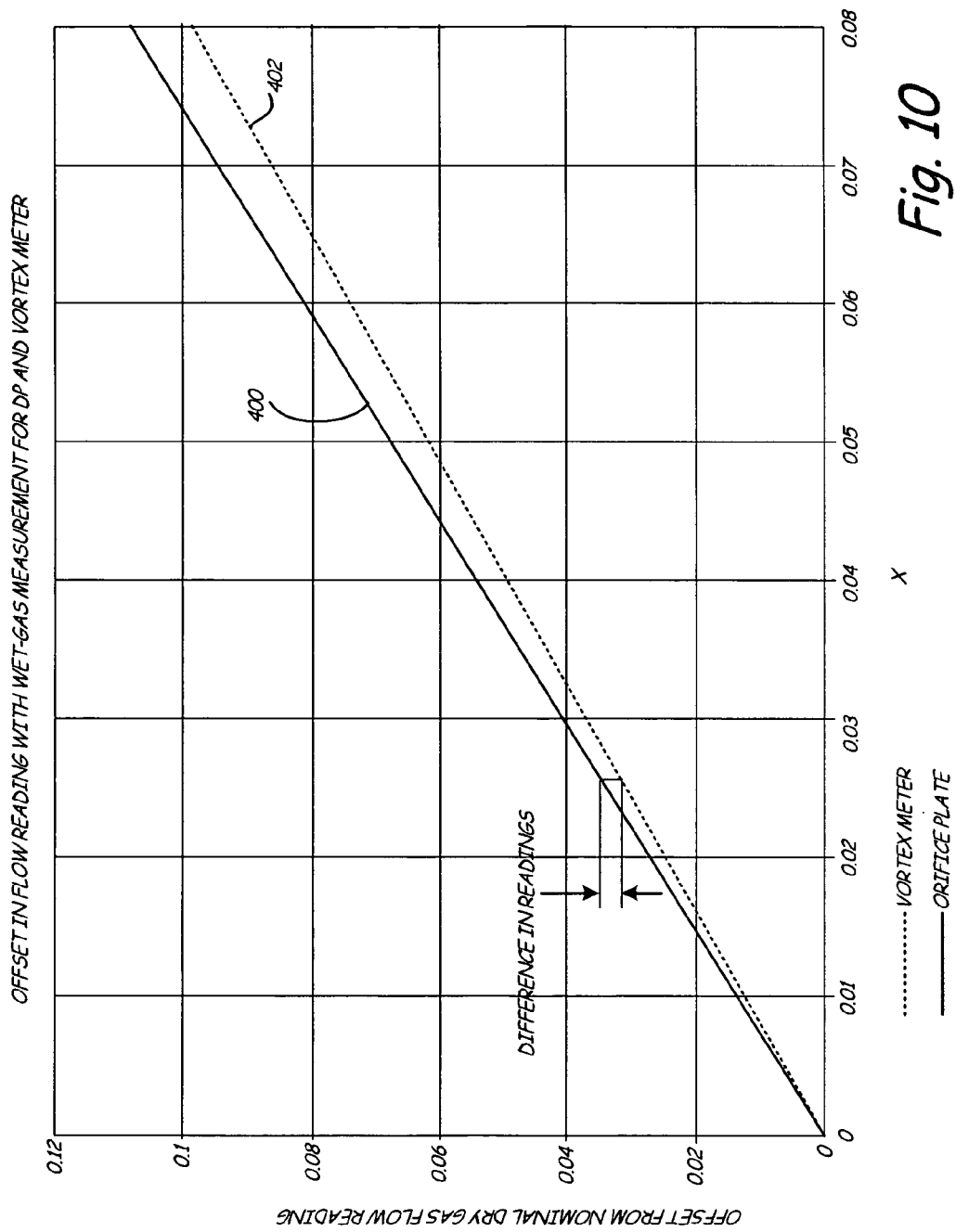
FIG. 10 is a chart showing offset in readings between differential pressure measurement and vortex flow measurement for varying steam quality (X).

This is an important feature especially with respect to steam mass flow and quality. To determine steam mass flow and quality using a vortex meter measuring differential pressure, temperature and volumetric flow, a $C_P$ for the differential pressure measurement should be known over a variety of mass flow and steam quality parameters. Similarly, the vortex meter flow should be characterized as a function of mass flow and steam quality. Assuming that the steam is not superheated, vapor and liquid phase densities can be calculated based on saturation properties at the measured temperature. Given this measured value and a $C_P = f(x,m)$, and a vortex flow where the vortex K-factor $K = f(x,m)$ where the x is steam quality and the m is mass flow, a system of two equations and two unknowns can accordingly be solved for the two unknowns. Solutions to these types of equations are performed today in a distributed control system, or similar location remote from the field device. In accordance with embodiments of the present invention, the field devices are now able to do this measurement in the field saving the customer money and providing higher quality information for control. FIG. 10 is a graph illustrating a difference in readings between an orifice plate reading and a vortex flowmeter reading 402 for varying steam quality X.

In accordance with another embodiment of the present invention, volumetric flow rate from a first field device can be used to tune, calibrate, or otherwise improve the operation and/or accuracy of the second field device. For example, volumetric flow rate can be determined by a differential pressure signal and fed back into the vortex flow measurement circuit and used to tune a notch filter in the vortex circuit. This feature can help address a problem particular to vortex sensing where the vortex signal is susceptible to background noise. By tuning the notch filter and digital signal processing based upon feedback from the differential pressure volumetric signal, the vortex measurement circuit is better able to track the actual vortex signal. Additionally, separate measurement of vortex and differential pressure flow enables diagnostics to be run that compare the two signals. For example, if the differential pressure-derived flow and the vortex-derived flow begin to diverge, an alarm or other suitable indication can be generated alerting the operator to a problem. This internal checking may be of particular interest in applications that employ safety implemented systems (SIS).

Although the present invention has been described with reference to preferred embodiments, workers skilled in the art will recognize that changes may be made in form and detail without departing from the spirit and scope of the invention.

What is claimed is:

1. A system for measuring mass flow of a process fluid in a pipe, the system comprising:
    a differential pressure measurement field device adapted to couple to the pipe, the differential pressure measurement field device having a differential pressure sensor to measure process fluid pressure upstream and downstream from a flow interrupter in the pipe;
    a fluid velocity device coupled to the pipe and adapted to sense a velocity of fluid flowing in the pipe; and
    fluid flow circuitry adapted to combine information from the differential pressure measurement field device and the fluid velocity device to provide an indication of a fluid flow property.

2. The system of claim 1, wherein the fluid flow property is density.

3. The system of claim 1, wherein the fluid flow property is mass flow.

4. The system of claim 1, wherein the fluid velocity device is a vortex sensing device.

5. The system of claim 1, wherein the fluid flow property is calculated by the differential pressure measurement field device.

6. The system of claim 1, wherein the field device communicates the fluid flow property in accordance with a process industry standard communication protocol.

7. The system of claim 1, wherein the fluid velocity device communicates with the differential pressure measurement field device.

8. The system of claim 7, wherein the communication is in accordance with a process industry standard communication protocol.

9. The system of claim 1, wherein the flow interrupter is shaped to generate vortices.

10. The system of claim 9, wherein the fluid velocity device senses a frequency of the vortices.

11. The system of claim 10, wherein the fluid velocity device includes a vortex displaceable member that is disposed downstream from the flow interrupter.

12. The system of claim 11, wherein the vortex displaceable member is coupled to a single side of the pipe.

13. The system of claim 12, wherein the vortex displaceable member includes a longitudinal beam and a thinned area for receiving pressure from a vortex.

14. The system of claim 13, wherein the vortex displaceable member further includes a transverse beam coupled to the longitudinal beam and the thinned area.

15. The system of claim 13, and further comprising a post coupleable to a piezoelectric sensing element such that displacements of the post are detected by the element.

16. The system of claim 1, and further comprising a temperature sensor disposed to provide an indication of process fluid temperature.

17. The system of claim 16, wherein the fluid flow property includes thermal mass flow.

18. The system of claim 16, wherein the fluid flow property is fluid composition.

19. The system of claim 16, wherein the fluid flow property is steam quality.

20. The system of claim 1, wherein the fluid velocity device is a vortex flowmeter field device.

21. The system of claim 1, wherein the differential pressure sensor is formed by a pair of pressure sensors, a first pressure sensor being disposed upstream from the interrupter, and a second pressure sensor being disposed downstream from the interrupter, and wherein at least one of the pair of pressure sensors is formed of a semiconductor material.

22. The system of claim 21, wherein at least one of the pressure sensors is disposed for direct contact with the process fluid.

23. The system of claim 21, wherein the semiconductor material is sapphire.

24. A system for measuring a property of a process fluid in a pipe, the system comprising:
a vortex sensing field device adapted to couple to the pipe and to measure a velocity of the fluid flowing in the pipe, the vortex sensing field device having a plurality of configurable terminations; and
wherein the vortex sensing field device calculates the property of the fluid based upon fluid velocity and a fluid variable measured through the plurality of configurable terminations.

25. The system of claim 24, and further comprising a switch coupled to the plurality of configurable terminations and to a microprocessor in the field device, wherein the microprocessor controls the switch to selectably couple the configurable terminations to an analog-to-digital converter in the vortex sensing field device.

26. The system of claim 24, and further comprising a fluid sensor operably coupled to the plurality of configurable terminations to provide an indication of the fluid variable.

27. The system of claim 26, wherein the fluid sensor is a differential pressure sensor disposed to measure differential pressure across a flow interrupter.

28. The system of claim 24, wherein the property of the process fluid is density.

29. The system of claim 24, wherein the property of the process fluid is mass flow.

30. The system of claim 26, wherein the fluid sensor is a pressure transmitter.

31. The system of claim 30, wherein the pressure transmitter is a differential pressure transmitter.

32. The system of claim 30, wherein the vortex sensing field device includes a resistor coupled across a communication loop of the pressure transmitter.

33. The system of claim 26, wherein the fluid sensor is disposed within a resistor bridge circuit.

34. The system of claim 26, wherein the vortex sensing field device provides power to the fluid sensor.

35. The system of claim 27, wherein the differential pressure sensor provides an indication of differential pressure to the vortex sensing field device in the form of a voltage.

36. The system of claim 26, wherein the vortex sensing field device and the fluid sensor communicate in accordance with a process industry standard communication protocol.

37. The system of claim 36, wherein the protocol is the Controller Area Network protocol.

38. The system of claim 24, wherein the vortex sensing field device communicates the fluid flow property in accordance with a process industry standard communication protocol.

39. The system of claim 27, wherein the vortex sensing field device includes a bluff body that generates and measures vortices in the flowing fluid, and wherein the differential pressure sensor measures a first pressure using a first pressure sensor disposed upstream from the bluff body, and a second pressure sensor disposed downstream from the bluff body.

40. The system of claim 24, and further comprising a temperature sensor operably coupled to the vortex sensing field device and disposed to provide an indication of process fluid temperature.

41. The system of claim 40, wherein the property of the process fluid is thermal mass flow.

42. The system of claim 40, wherein the property of the process fluid is fluid composition.

43. The system of claim 40, wherein the property of the process fluid is steam quality.

44. The system of claim 27, wherein the differential pressure sensor comprises a pair of pressure sensing elements, each element being formed of a semiconductor material.

45. The system of claim 44, wherein the semiconductor material is sapphire.

46. The system of claim 27, wherein the differential pressure sensor is disposed for direct contact with the process fluid.

47. The system of claim 24 wherein the vortex sensing field device is adapted to couple through the plurality of configurable terminations to a fluid sensor selected from the group consisting of an absolute pressure sensor, a gage pressure sensor or a differential pressure sensor.

48. A field device for sensing mass flow of a process fluid in a pipe, the field device comprising:
a vortex generator positionable in the pipe to generate vortices in the fluid as the fluid flows;
a first pressure sensor disposed upstream from the vortex generator to sense an upstream fluid pressure;
a second pressure sensor disposed downstream from the vortex generator, the second pressure sensor providing an indication of vortices and downstream pressure, the second pressure sensor having a plurality of configurable terminations; and
wherein the field device calculates differential pressure from the first and second pressure sensor signals, and calculates vortex frequency from the second pressure sensor signal.

49. The system of claim 48, wherein at least one of the first and second pressure sensors is formed of a semiconductor material.

50. The system of claim 48, wherein at least one of first and second pressure sensors is disposed for direct contact with the process fluid.

51. The system of claim 48, wherein the semiconductor material is sapphire.

52. A method of measuring flow of a process fluid flowing in a pipe with a field device, the method comprising:
provided a flow interrupter in the fluid;
sensing a differential pressure between upstream and downstream locations from the interrupter, through a configurable interface;
measuring fluid velocity; and
calculating, in the field device, mass flow of the fluid based upon the differential pressure and the measured velocity.

53. A method of adjusting a vortex flowmeter having a notch filter, the method comprising:
obtaining a fluid flow rate measurement using the vortex flowmeter;
obtaining a fluid flow measurement using a differential pressure measurement field device; and
adjusting the notch filter of the vortex flowmeter such that the vortex-measured rate matches the differential-pressure measured rate.

54. A method of providing diagnostics relative to a process fluid measurement system, the method comprising:
generating a first process fluid flow rate output with a vortex flowmeter field device coupled to a pipe containing process fluid, the vortex flowmeter field device having a plurality of configurable terminations;
generating a second process fluid flow rate output with a differential pressure flowmeter field device coupled to the pipe; and
comparing the first and second outputs and generating a diagnostic output based upon the comparison.

55. A system for measuring a property of a process fluid in a process fluid container, the system comprising:
a differential pressure measurement field device coupled to the process fluid container, the differential pressure measurement field device for measuring differential pressure across a flow interrupter in the conduit;
means for measuring process fluid velocity coupled to the conduit to sense a velocity of fluid flowing in the conduit, the means for measuring process fluid velocity having a plurality of configurable terminations; and
wherein differential pressure and measured velocity are combined to provide an indication of the property.

56. A field device for sensing a property of a process fluid in a pipe, the field device comprising:
a vortex generator positionable in the pipe to generate vortices in the fluid as the fluid flows;
a vortex sensor disposed to detect the vortices in the fluid;
a controller operably coupled to the vortex sensor to calculate fluid flow rate based on detection of vortices in the fluid by the vortex sensor;
an analog-to-digital converter having an output coupled to the controller;
a plurality of configurable terminations coupled to the controller and to an input of the analog-to-digital converter, the terminations receiving a first input from a fluid sensor to allow the controller to selectively couple the first input to the analog-to-digital converter; and
wherein the controller is configured to calculate the process fluid property based upon the fluid flow rate and a fluid variable measured by the fluid sensor through the configurable terminations.

57. The field device of claim 56, wherein the fluid sensor is a differential pressure sensor disposed to measure differential pressure across a flow interrupter in the pipe.

58. The field device of claim 56, wherein operating power for the differential pressure sensor is provided through the switch.

59. The field device of claim 56, and further comprising a temperature sensor coupled to a third input of the switch, the temperature sensor configured to provide an indication of process fluid temperature to the controller through the switch.

60. The field device of claim 56, wherein the fluid property is selected from the group consisting of mass fluid flow, fluid density, heat content, heat flow, fluid quality and fluid composition.

61. The field device of claim 56 wherein the field device is adapted to couple through the plurality of configurable terminations to a pressure sensor or a differential pressure sensor.

* * * * *